(12) United States Patent
De Zayas

(10) Patent No.: US 11,266,794 B2
(45) Date of Patent: Mar. 8, 2022

(54) ARM RESTRAINT FOR IV SITE STABTILITY

(71) Applicant: Comfort Boards, LLC, Haines City, FL (US)

(72) Inventor: Cheryl De Zayas, Haines City, FL (US)

(73) Assignee: Comfort Boards, LLC, Pensacola, FL (US)

( * ) Notice: Subject to any disclaimer, the term of this patent is extended or adjusted under 35 U.S.C. 154(b) by 864 days.

(21) Appl. No.: 15/686,124

(22) Filed: Aug. 24, 2017

(65) Prior Publication Data

US 2018/0110937 A1    Apr. 26, 2018

Related U.S. Application Data

(63) Continuation of application No. 14/653,309, filed as application No. PCT/US2013/076081 on Dec. 18, 2013, now abandoned.

(60) Provisional application No. 61/738,504, filed on Dec. 18, 2012.

(51) Int. Cl.
*A61M 5/52* (2006.01)
*A61F 5/37* (2006.01)

(52) U.S. Cl.
CPC .............. *A61M 5/52* (2013.01); *A61F 5/3761* (2013.01)

(58) Field of Classification Search
CPC ................ A61M 5/52; A61M 25/02; A61M 2025/0206; A61M 2025/0213; A61M 2025/0253; A61M 2025/026; A61M 2025/028; A61M 25/01; A61F 5/04; A61F 5/05; A61F 5/058; A61F 5/05825; A61F 5/05841–05875; A61F 5/37; A61F 5/3761; A61F 5/3769; A61F 5/3792; A61F 5/01; A61F 5/05858; A61F 5/05866; A61F 5/05875; A61F 5/3715; A61F 5/3723; A61F 5/373; A61F 5/3776
See application file for complete search history.

(56) References Cited

U.S. PATENT DOCUMENTS

| 2,693,794 A | * | 11/1954 | Neville | A61M 5/52 600/499 |
| 4,489,716 A | * | 12/1984 | Blackwood | A61F 5/373 602/20 |
| 4,960,114 A | * | 10/1990 | Dale | A61F 5/05866 602/21 |
| 4,977,890 A | * | 12/1990 | Mann | A61F 5/05866 602/21 |
| 5,413,554 A | * | 5/1995 | Trueman | A61F 5/05866 482/48 |

(Continued)

*Primary Examiner* — Michelle J Lee
(74) *Attorney, Agent, or Firm* — Law Office of Oliver Edwards LLC; Oliver Edwards

(57) ABSTRACT

The invention relates to an upper extremity restraint which uses moveable non-adhesive restraint strappings and a reversible rigid platform, which enables a caregiver to ensure the patient's secure upper limb positioning for intravenous site maintenance. The present invention also includes an upper extremity restraint which uses parallel openings in the backbone restraint, which enable the immobilization of the upper limb through use of tie down restraining to prevent formation of hematomas or other types of patient injury caused by IV catheter site interruption or displacement.

22 Claims, 6 Drawing Sheets

(56) References Cited

U.S. PATENT DOCUMENTS

| | | | | |
|---|---|---|---|---|
| 2004/0138597 | A1* | 7/2004 | Varn | A61F 5/05866 602/21 |
| 2004/0225241 | A1* | 11/2004 | Scheinberg | A61F 5/0118 602/5 |
| 2005/0080369 | A1* | 4/2005 | Kim | A61F 5/05858 602/12 |
| 2005/0234374 | A1* | 10/2005 | Grim | A61F 5/05841 602/6 |

* cited by examiner

ARM RESTRAINT FOR IV SITE STABTILITY

This application is a continuation of application Ser. No. 14/653,309, a national stage entry of PCT/US2013/076081 filed Dec. 18, 2013, which claims the benefit of provisional application 61/738,504 filed Dec. 18, 2012.

TECHNICAL FIELD

The present invention relates to an upper extremity restraint which may be worn by a patient while receiving treatment provided by a healthcare practitioner. More specifically, it relates to an upper extremity restraint useful for providing stability for intravenous (IV) sites on the patient's distal upper extremity and also for decreasing upper extremity movements.

When a medical practitioner administers treatment to a patient, she oftentimes must stabilize the patient's upper limb in order to successfully complete certain prescribed procedures. One such procedure is the maintenance of an IV needle insertion site on the patient's distal upper extremity. For example, medical practitioners typically insert the IV needle into the dorsum of the patient's hand or the patient's antecubital area. Maintenance of the IV needle insertion site is necessary for continuous and uninterrupted transfer of IV fluids including, but not limited to, crystalloids, colloids, blood and blood products, which flow out of a pouch held at the patient's side and into the patient's circulatory system. A patient's upper extremity movement, however, often causes IV catheter dislodgement and possible patient injury, thereby interrupting patient IV therapy. Additionally, some post-surgical procedures, such as cardiac catheterization, angiographies, etc., require restraining the patient's extremity movement. Movements unchecked may cause the development of unwanted hematomas in the patient or other types of patient injury caused by IV catheter site interruption or displacement. In all of these procedures, the caregiver's overriding concern is that the patient's upper limb is stabilized in a comfortable position throughout the procedure duration.

Heretofore, upper arm restraints for IV insertions have been typically limited to facilitate catheter insertions into the dorsum of the hand; see for example U.S. Pat. Nos. 4,043,330, 5,018,534, 5,083,575, 5,339,834, 5,682,905 and 7,077,142. Such restraints are limited in that they may cover the patient's antecubital area and prevent IV catheter insertions at this location. If such conventional restraints allow for sufficient exposure of a patient's antecubital area, the restraint may still not prevent a patient's elbow movements, thereby causing IV catheter dislodgement and possible injurious effects.

Prior versions of upper arm restraints also implemented the use of adhesive tape or strapping to restrain the upper limb onto a rigid support board. These strappings, unfortunately, have led to patient injuries, including the loss of hair and tearing of skin at locations where the tape adhered directly to the patient's skin. Worse yet, The Joint Commission (TJC), formerly the Joint Commission on Accreditation of Healthcare Organizations (JCAHO), has documented twenty-five incidents in which pediatric patients have suffered from traumatic amputation of a digit or portion thereof after a caregiver attempted to remove adhesive strappings using cutting means. This unintended severe trauma to distal portions of digits occurs most frequently when adhesive strappings obscure the location of a pediatric patient's fingers.

Adhesive tape or strapping is also deficient for use in securing upper extremity restraints because it is not easily removable and, consequently, does not allow the practitioner to readily detect the formation of edema or discoloration in a patient's extremity. These strappings, moreover, do not allow the practitioner to easily remove the upper extremity restraint for regular cleaning of the patient's extremity and regular cleaning of the restraint itself.

In an attempt to overcome the problems caused by use of adhesive strapping for restraint of pediatric upper limbs, the restraint described in U.S. Pat. No. 7,077,412 discloses use of a rigid support board attached to a flexible netting. As disclosed, this netting is stretched over the pediatric patient's arm and hand, thereby protecting the inserted IV catheter and allowing for visual inspection of the IV site. TJC, however, has mandated that it will no longer allow such netting, kurlex, gauze or other forms of wrapping over the arm and hand as a result of the described incidence of severed digits. Because TJC accredits more than 19,000 health care organizations and programs in the United States alone, healthcare practitioners are, thus, in need of viable alternatives to upper arm restraints which do not employ netting or other forms of wrapping over the arm.

Another version of an upper arm restraint, the AVCOR All-In-One® I.V. Arm Support System, utilizes non-adhesive strapping, which eliminates the need for taping. However, the product's non-adhesive strappings are moveable on only one end of each strapping's two ends. Thus, options are limited for adjusting the arm strapping for optimal patient comfort and IV catheter stability. Additionally, this product utilizes a semi-rigid cardboard constructed with a solid piece of crepe material with fine hooked ends used to secure the arm strappings, however, they cannot fully control the movement of the patient. Moreover, the armboard has a high degree of flexibility such that the patient can easily remove his arm through the proximal end of the armboard, thereby endangering the integrity of the IV catheter site on the distal portion of the limb.

Accordingly, a need exists for an upper extremity restraint worn by a patient that maintains the integrity of an IV catheter site or other localized therapy, at either the dorsum of the hand or the antecubital area, through stable and rigid limb support and secure strapping, while maintaining patient comfort. It is highly desirable that such strapping should be easily removable to allow practitioner detection of patient edema or discoloration, allow easy cleaning of the patient's extremity, and allow easy cleaning of the upper extremity restraint, itself. Furthermore, there is a need for an upper extremity restraint wearable by a pediatric patient which does not obscure a pediatric patient's digits through the use of netting or other forms of wrapping over the arm. Lastly, a need exists for an upper extremity restraint wearable by a patient which can also decrease upper extremity movements and prevent the formation of patient hematomas or other types of patient injury caused by IV catheter site interruption or displacement.

DISCLOSURE OF THE INVENTION

Accordingly, the limitations and problems as just described are obviated according to embodiments of the present invention which include an upper extremity restraint which uses moveable non-adhesive restraint strappings and a reversible rigid platform capable of conforming to several upper extremity configurations, which, in total, enables versatile upper limb positioning for IV site maintenance.

Some embodiments may also include perforations in the rigid platform, which enable immobilization of the upper limb through use of tie down restraining to prevent formation of hematomas or other types of patient injury caused by IV catheter site interruption or displacement.

BRIEF DESCRIPTION OF THE DRAWINGS

For a comprehensive exposure of the features, nature and advantageous effects of the present invention, reference is now made to the detailed description in conjunction with the associated drawings, in which.

MODES FOR CARRYING OUT THE INVENTION

Embodiments of the present invention may be used to restrain the upper extremity, either proximal or distal sections or combinations thereof, including but not limited to hand, wrist, lower arm, upper arm and shoulder. Embodiments of the present invention are also useful for providing stability to IV catheterization sites and to decrease extremity movements. Restraint of the upper extremity is particularly desirable when IV therapy continues post-surgical procedure, e.g., post-cardiac catheterization, angiographies, etc. Embodiments of the present invention may also be used in any non-surgical situation that requires maintaining the integrity of an IV insertion placement. For example, such situations may include, but are not limited to when a patient experiences trauma, seizures, intoxication, tremors, delirium, etc.

Figure 1:
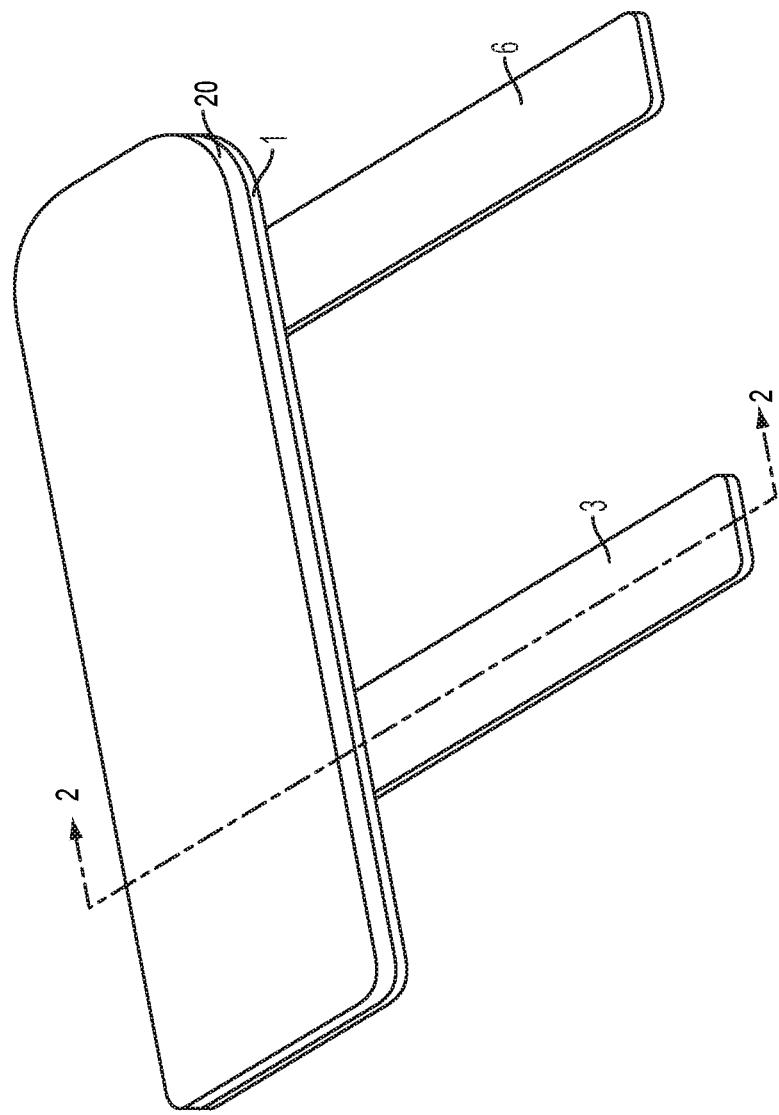
FIG. 1 is a perspective view of a newborn or pediatric sized upper extremity restraint in accordance with an exemplary embodiment of the invention wherein non-adhesive strappings are in an open position.

Referring to FIG. 1, the upper extremity restraint of the present invention may be sized to fit newborn and pediatric patients.

In an exemplary embodiment for newborn patients, an elongated rectangular upper arm restraint backbone 1 measures about 1.5 to 2 inches in width, about 4.5 to 5.5 inches in length and 2-6 mm in thickness. In a preferred embodiment, the newborn sized upper extremity restraint measures approximately 1.75 inches in width, 5 inches in length and 4 mm in thickness.

In an exemplary embodiment for pediatric patients, an elongated rectangular upper arm restraint backbone 1 measures about 1.5 to 2 inches in width, 7.5 to 8.5 inches in length and 2-6 mm in thickness. In a preferred embodiment, the pediatric sized upper extremity restraint measures approximately 1.75 inches in width, 8 inches in length and 4 mm in thickness.

Corners of the backbone 1 may be rounded off to prevent sharp corners from causing patient discomfort or injury. In a preferred embodiment, the backbone 1 may be substantially oblong in shape. The restraint backbone 1 may be made of any rigid or semi-rigid substance. The restraint backbone 1 may be solid or perforated for added ventilation. Examples of backbone 1 materials include, but are not limited to, plastic, plaster, resins, wood, metal, polycarbonates, etc. The restraint backbone 1 may be coated with an anti-microbial component, thereby improving patient hygiene, minimizing infection risk and preventing odors caused by bacteria. In a preferred embodiment, the restraint backbone 1 is constructed with a thermoplastic moldable material.

Figure 2:
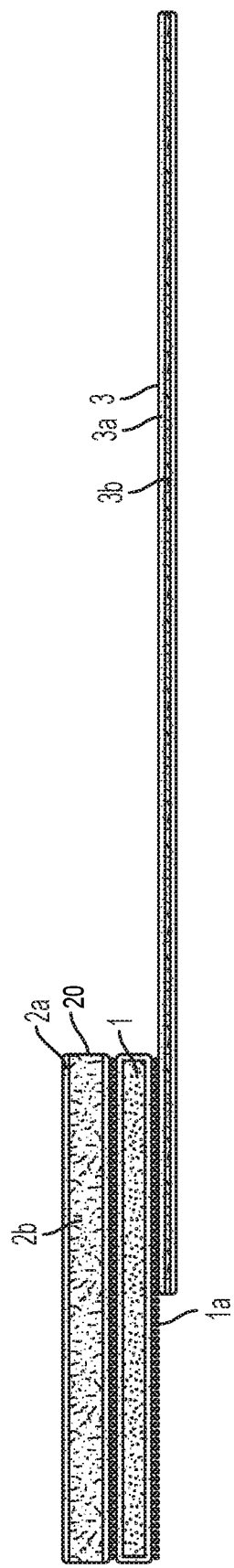
FIG. 2 is a cross-sectional view of a newborn sized upper extremity restraint on lines 2-2 of FIG. 1 in accordance with an exemplary embodiment of the invention wherein the non-adhesive strappings are in an open position.

Referring to FIG. 2, the upper extremity restraint in accordance with embodiments of the present invention may include Velcro type hook fastener 1*a* sites located on anterior and/or posterior sides of the restraint backbone 1. As recognized by those of skill in the art, anterior side means the side of the restraint backbone 1 facing the patient's appendage. Further recognized by the skilled artisan, the posterior side means the side of the restraint backbone 1 facing away from the patient's appendage. In a preferred embodiment, the hook fastener 1*a* sites are smooth to the touch and non-abrasive. The hook fastener 1*a* sites may comprise the anterior and/or posterior surfaces of the restraint backbone 1 completely or partially. Alternatively, the hook fastener 1*a* sites may be placed on the edges of the restraint backbone 1. In a preferred embodiment, the complete surface of the restraint backbone 1 on both the anterior and posterior surfaces is covered in hook fastener 1*a* material. In a further preferred embodiment, the Velcro type hook fastener 1*a* material is a sheet which may be attached to both the anterior and posterior surfaces of the restraint backbone 1 by an adhesive layer on the hook fastener material 1*a* base, although other means of affixing the Velcro type hook fastener 1*a* material to both the anterior and posterior surfaces of the restraint backbone 1 may be used and are considered within the scope of the invention.

Referring to FIG. 2, areas of the top or anterior surface of the restraint backbone 1, which are covered partially or completely with a sheet of Velcro type hook fastener material 1*a*, may be covered either partially or completely with therapy material 20. Most preferably, the anterior surface is covered completely with therapy material 20 and all edges trimmed such that the material is flush with oppositely disposed side edges of the restraint backbone 1. Suitable materials for therapy material 20 in accordance with embodiments of the present invention include, but are not limited to elastic, knit, fabric, foam, hypoallergenic or any combination of these suitable materials. In a preferred embodiment, the therapy material 20 consists of a central foam sheet layer 2*b* with a smooth fabric layer 2*a* or lining affixed to both sides of the foam sheet. In a preferred embodiment, the therapy material 20 serves as complementary loop fastener material 2*a* and attaches securely to Velcro type hook fastener 1a sites located and affixed to the anterior side of the restraint backbone 1. Within the scope of the invention, either side of the restraint backbone 1 may be covered in therapy material 20, thereby facilitating upper extremity restraint versatility through restraint backbone 1 reversibility. In a preferred embodiment, areas of therapy material 20 in direct contact with the patient's skin are covered with a smooth fabric lining 2a to maximize patient comfort. Additionally, the foam layer 2b of the therapy material 20 may serve as a cushion between the patient's skin and the anterior surface of the rigid restraint backbone 1, thereby preventing pressure sores by providing a comfort layer.

Figure 3:
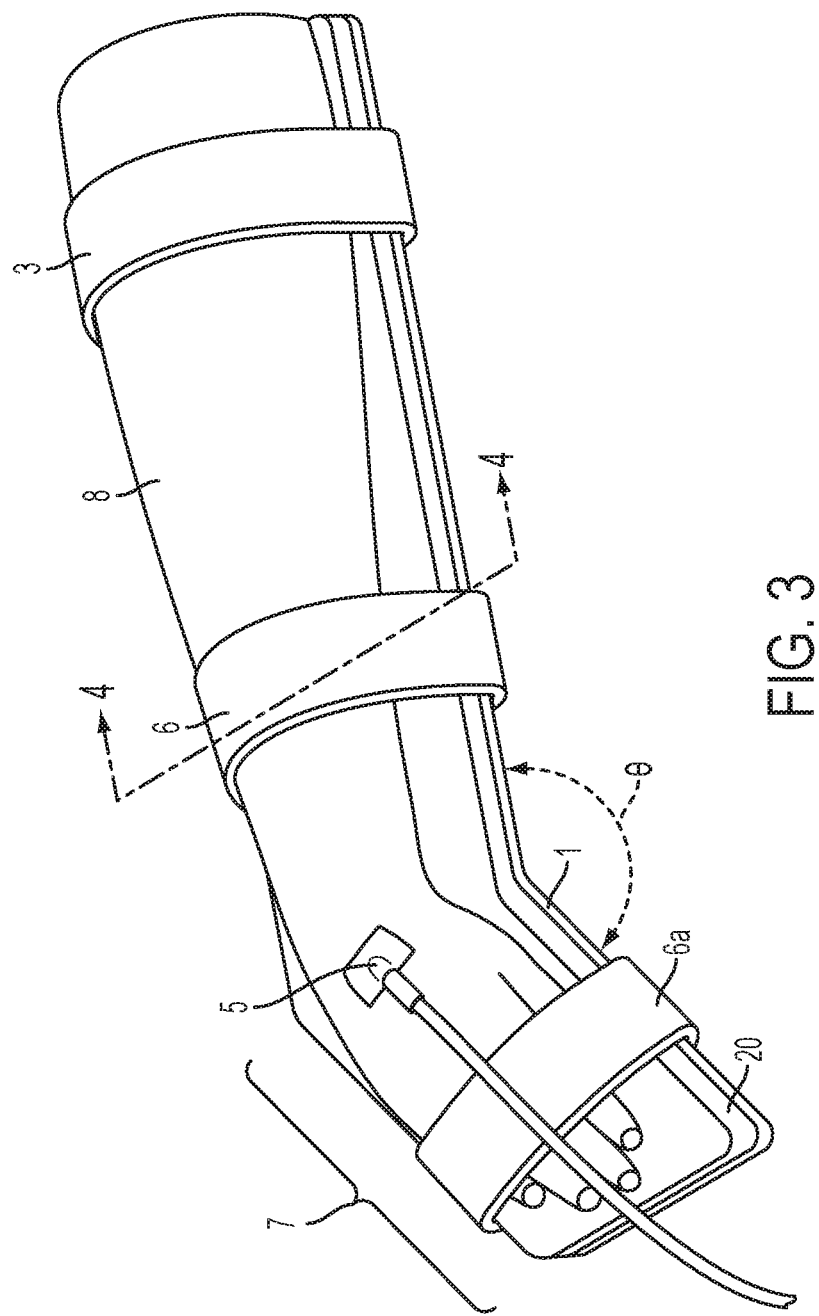
FIG. 3 is a perspective view of a child sized upper extremity restraint in accordance with an exemplary embodiment of the invention wherein the distal end is configured to restrain and expose the dorsum of the patient's hand for IV catheter insertion or other therapy.
Figure 4:
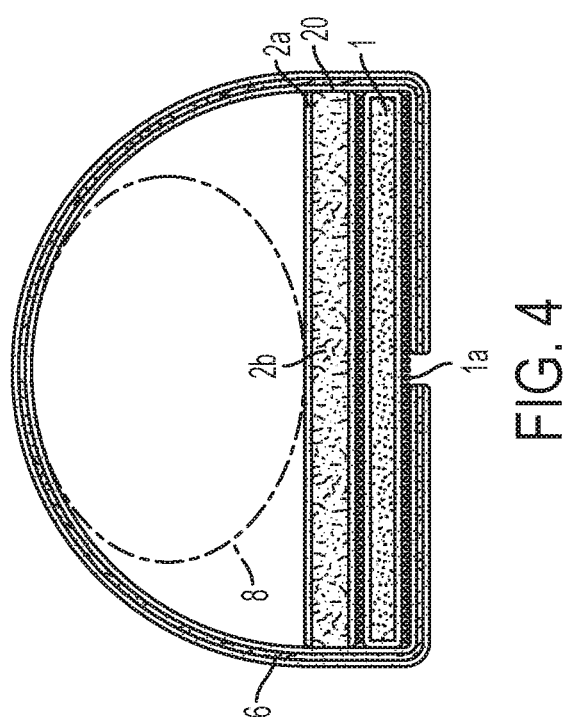
FIG. 4 is a cross-sectional view of a child sized upper extremity restraint on lines 4-4 of FIG. 3 in accordance with an exemplary embodiment of the invention wherein non-adhesive straps are in a closed position to restrain the patient's arm.

Referring to FIGS. 2 and 3, the hook fastener sites 1a located on the posterior side of the restraint backbone 1 enables fastening of non-adhesive strapping. In a preferred embodiment, the hook fastener 1a site covers the posterior of the restraint backbone 1 completely, thereby facilitating the placement of anterior strappings at the proximal 3 and distal 6, 6a ends with complementary loop fasteners 3a anywhere on the posterior of the restraint backbone 1 according to the needs of the patient. Thus, anterior strapping fastening may occur anywhere and in any combination on the edges or posterior aspects of the restraint backbone 1, thereby facilitating secure maintenance of extremity position and patient comfort. In a preferred embodiment, as illustrated in FIG. 4, anterior strapping fastening occurs on the posterior aspects of the restraint backbone 1, with anterior strapping extending continuously from both of the restraint backbone 1 side edges. Because the strapping can be placed and replaced to remove any strapping slackness without having to completely restructure the positioning, the risk of unintended consequences, particularly IV catheter disengagement, interruption and concomitant patient injury, is greatly reduced.

Referring to FIG. 3, suitable materials for non-adhesive strapping 3, 6, 6a in accordance with embodiments of the present invention include, but are not limited to, elastic, knit, fabric, foam or any combination of these suitable materials. In a preferred embodiment, the strappings consist of a central foam sheet layer 3b with a smooth fabric layer 3a or lining affixed to both sides of the foam sheet, as illustrated in FIG. 2.

Referring to FIGS. 2, 3 and 4, restraint of the patient's upper extremity 8 is facilitated by fixation of the anterior strapping's smooth fabric loop fasteners 3a to the complementary Velcro type hook fasteners 1a located on the posterior side of the restraint backbone 1. In a preferred embodiment, each end of the anterior strapping 3, 6 and 6a is adjustable and may be placed on the complementary hook fastener 1a accordingly to maximize restraint of the patient's upper extremity 8, while maintaining patient comfort. If the initial anterior strapping end placement fails to achieve optimal upper extremity restraint and/or provides discomfort to the patient, strapping end placement can be easily relocated accordingly.

Strapping length and width may be adjusted according to the needs of the patient, namely comfort while maintaining secure restraint of the upper extremity. For example, adult patients may require longer strappings to accommodate larger extremity girth and width. Embodiments of the invention allows for easy removal of each strapping and, thus, the entire upper extremity restraint, in order to detect patient extremity edema or discoloration. Thus, the inventive design allows for easy removal and repositioning of the non-adhesive strappings based on the patient's needs.

The inventive design further allows easy cleaning of the patient's hand and arm, as well as the upper extremity restraint itself. In the event that therapy material and/or strapping becomes soiled with blood, intravenous fluid or other contaminants, the materials and/or strapping may simply be removed and replaced with new and clean therapy material and/or strapping.

Referring to FIG. 3, embodiments of the present invention may facilitate IV catheter insertions into the dorsum 5 of the patient's hand. The distal end 7 may comprise a curve or bend to maintain a neutral position of the fingers of the patient's hand. In a preferred embodiment, the degree of bend fore ranges from 85°-175°, most preferably 135°.

The upper extremity restraint configured for IV catheter insertions into the dorsum 5 of the hand of the present invention may be sized to fit child patients. In exemplary embodiments for child patients, the portion of the upper arm restraint backbone 1 supporting the patient's forearm to wrist measures about 6-10 inches in length, the portion of the restraint backbone 1 supporting the patient's wrist and hand measures about 2-6 inches in length, and the restraint backbone 1 measures 2-5 inches in width and 0.025-0.225 inches in thickness. In a preferred embodiment for this configuration, the portion of the upper arm restraint backbone 1 supporting the patient's forearm to wrist measures about 8 inches in length, the portion of the restraint backbone 1 supporting the patient's wrist and hand measures about 4 inches in length, and the restraint backbone 1 measures 3 inches in width and 0.125 inches in thickness. Also within the scope of the invention is the patient's use of the opposite or reverse side of the restraint backbone 1.

Figure 5:
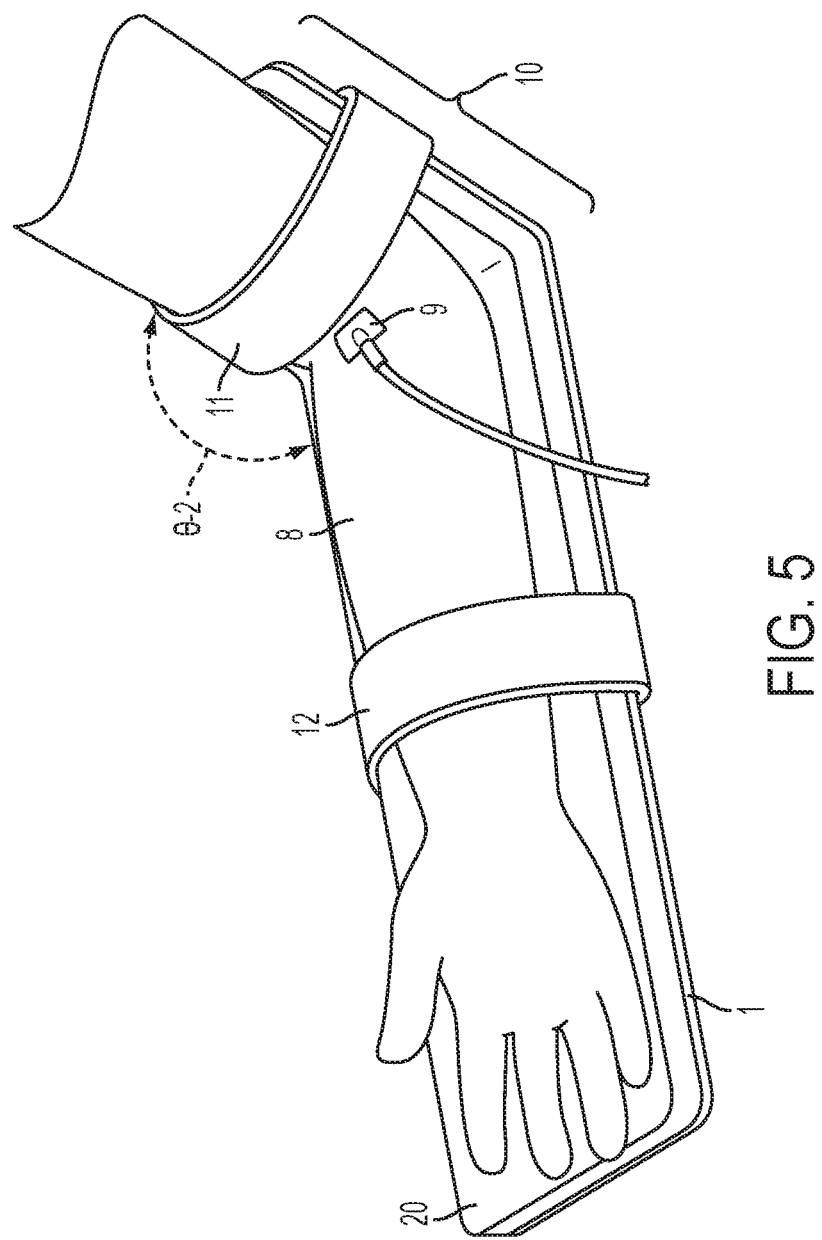
FIG. 5 is a perspective view of a child sized upper extremity restraint in accordance with an exemplary embodiment of the invention wherein the proximal end is configured to restrain and expose the antecutibal area of the patient's arm for IV catheter insertion or other therapy.

Referring to FIG. 5, the upper extremity restraint of the present invention may be modified to facilitate IV catheter insertions into the patient's antecubital area 9. The proximal end may comprise a curve or bend forming a relaxed backstop to maintain the patient's upper extremity elbow position within the restraint. As such, the backstop 10 functions to restrict the patient's ability to slide her forearm out the proximal end of the restraint, thereby maintaining the integrity of an IV catheterization site on the patient's antecubital area 9. In a preferred embodiment, the degree of bend for θ-2 ranges from 85°-175°, most preferably 145°.

The upper extremity restraint configured for IV catheter insertions into the antecubital area of the present invention may be sized to fit child patients. In exemplary embodiments for child patients, the portion of the restraint backbone 1 supporting the patient's elbow and upper arm measures about 2-6 inches in length, the portion of the upper arm restraint backbone 1 supporting the patient's elbow to forearm measures about 6-10 inches in length, and the restraint backbone 1 measures 2-5 inches in width and 0.025-0.225 inches in thickness. In a preferred embodiment for this configuration, the portion of the restraint backbone 1 supporting the patient's elbow and upper arm measures about 4 inches in length, the portion of the upper arm restraint backbone 1 supporting the patient's elbow to forearm measures about 8 inches in length, and the restraint backbone 1 measures about 3 inches in width and 0.125 inches in thickness. Also within the scope of the invention is the patient's use of the opposite or reverse side of the restraint backbone 1.

Referring to FIGS. 3 and 5, in an exemplary embodiment for an upper extremity restraint configured for either dorsum or antecubital IV insertions, the upper arm restraint may have anterior strapping 3, 11 at the proximal end and anterior strapping 6, 6a, 12 at the distal end. Each anterior strapping may be constructed with smooth fabric fasteners at both ends. Fixation of each anterior strapping's smooth fabric loop fastener 3a ends to the complementary Velcro type hook fasteners 1a located on the posterior side of the restraint backbone 1, facilitates both upper extremity restraint and patient comfort.

In an exemplary embodiment for an upper extremity restraint configured for either dorsum or antecubital IV insertions, the patient's upper extremity rests may rest comfortably on therapy material 20, which is affixed to the restraint backbone 1 via Velcro hook fasteners sites 1a on the restraint backbone's 1 patient facing anterior side. Thereby, in the upper extremity restraint configured for dorsum IV insertions, the patient's fingers may be gently and comfortably restrained in a neutral position at the curved distal end 7 of the restraint. In the upper extremity restraint configured for antecubital IV insertions, the inventive design allows the patient's elbow to be gently restrained comfortably at the curved proximal end 10 of the restraint. Also within the scope of the invention is the patient's use of the opposite or reverse side of the restraint backbone 1.

Figure 6:
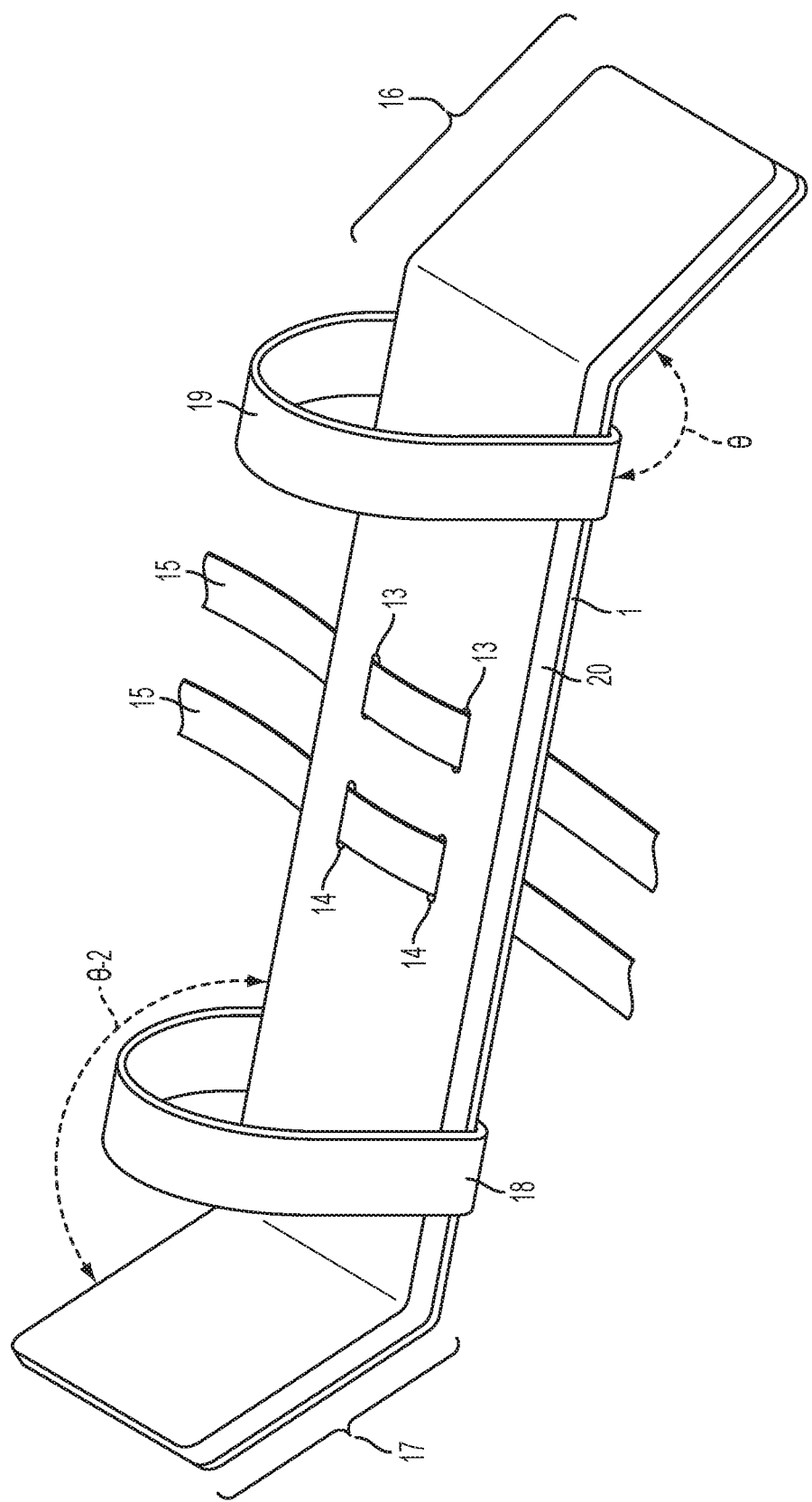
FIG. 6 is a perspective view of an adult sized upper extremity restraint in accordance with an exemplary embodiment of the invention wherein the distal end is configured to restrain and expose the dorsum area of the patient's hand for IV catheter insertion and the proximal end is configured to restrain and expose the antecubital area of the patient's arm for IV catheter insertion or other therapy.

Referring to FIG. 6, within the scope of the present invention are embodiments of upper extremity restraints sized to fit larger teenagers and adults. In a preferred embodiment for this size configuration, the inventive design allows for one end 16 of the upper extremity restraint to be utilized for IV catheter insertions into the dorsum of the hand. Alternatively, if the caregiver prefers to insert an IV catheter into the patient's antecubital area, the other end 17 of the upper extremity restraint may be utilized. Also within the scope of the invention is the patient's use of the opposite or reverse side of the restraint backbone 1.

In exemplary embodiments for upper extremity restraints sized to fit larger teenagers and adults, the restraint backbone 1 measured from end to end is about 3-5 inches in width and about 22-26 inches in length, and preferably 4 inches in width and 24 inches in length. In exemplary embodiments for this configuration, the upper extremity restraint may measure about 0.025-0.225 inches in thickness and, most preferably, 0.125 inches in thickness.

In exemplary embodiments, the flat central portion of the teenager and adult sized configuration which supports the patient's forearm may measure 8-12 inches in length and, preferably, 10 inches in length.

The distal end 16 may be curved or bent downward downwards relative to the anterior surface to maintain a neutral position of the fingers of the patient's hand (not shown). In a preferred embodiment, the degree of bend for θ ranges from 85°-175°, most preferably 135°. In a preferred embodiment for this configuration, the portion of the restraint backbone 1 supporting the patient's wrist and hand measures about 2.5-6.5 inches in length, and, most preferably, 4.5 inches in length.

In another preferred embodiment of this configuration, the proximal end 17 is bent or curved upwards relative to the anterior surface to maintain the patient's upper extremity elbow position within the restraint. As such, the bend or curve at 17 functions to restrict the patient's ability to slide her forearm out the proximal end of the restraint, thereby maintaining the integrity of an IV catheterization site on the patient's antecubital area. In a preferred embodiment, the degree of bend for θ-2 ranges from 85°-175°, most preferably 145°. In a preferred embodiment for this configuration, the portion of the restraint backbone 1 supporting the elbow and upper arm measures about 2.5-6.5 inches in length, and, most preferably, 4.5 inches in length.

In an exemplary embodiment, the upper arm restraint may have anterior strapping 18 at the proximal end and anterior strapping 19 at the distal end. Each anterior strapping, 18 and 19, may be constructed with smooth fabric loop fasteners 3a at both ends. Fixation of each anterior strapping's 18 and 19 fabric loop fastener 3a ends to the complementary Velcro type hook fasteners 1a located on the posterior side of the restraint backbone 1, facilitates both upper extremity restraint and patient comfort, thereby gently restraining the fingers comfortably in a neutral position at the curved distal end 16 of the restraint and gently restraining the elbow in a relaxed comfortable position at the curved proximal end 17. The present invention may also be made with one or more additional anterior strappings (not shown). In this embodiment, restraint of the patient extremity may be achieved through use of the proximal backstop strapping 18, a second distal anterior strapping 19, a third anterior strapping around the distal end 16 and a fourth anterior strapping around the proximal end 17. An exemplary embodiment of the use of three anterior strappings is illustrated in FIG. 3.

As pictured in FIG. 6, parallel openings 13, 14 in the restraint backbone 1 allow a full restraint of a combative, incompetent or obstreperous patient without risking the formation of hematomas or other types of patient injury caused by IV catheter site interruption or displacement. This is achieved through use of tie down restraining 15 in accordance with an exemplary embodiment of the invention. The parallel openings 13, 14 may be made by perforating, drilling, molding or cutting the restraint backbone 1 and the therapy material 20 to create slots which run parallel to the patient's extremity. In another embodiment, the parallel openings 13, 14 may be made only in the backbone 1 and not the therapy material 20 (not illustrated). In a preferred embodiment for a teenager or adult-sized upper extremity restraint, two or more pairs of parallel openings, most preferably two pairs, may facilitate use of tied down restraints. Each slot may begin approximately 6 inches from the ends of the flat central portion of the teenager and adult sized configuration which supports the patient's forearm. Each parallel slot may be dimensioned to accommodate the insertion of tie down strapping 15 through the slot openings. For example, a slot length of 1 inch in length and 0.13 inches in width may be sued to accommodate 0.9 inch width of tied down strapping. Each parallel slot may be located at a distance from the edge of the restraint backbone 1 that is approximately one-fourth the width of the restraint backbone 1. In an exemplary embodiment, as shown in FIG. 5, a tie down strapping 15 secured to a hospital gurney (not shown), for example, may be slotted through the parallel openings 13, 14 to secure a non-compliant patient to the gurney. Within the scope of the invention are embodiments in which a tie down strapping 15 may be slotted through the parallel openings 13, 14 to secure a non-compliant patient to a variety of patient stations.

In a preferred embodiment for a child sized upper extremity restraint, one or more pairs of parallel openings, most preferably one pair, may facilitate use of tied down restraints. In a preferred embodiment for a child sized upper extremity restraint, each parallel opening may begin approximately 3.5 inches from the end of the restraint backbone 1. Each parallel slot may measure, for example, 1 inch in length and 0.13 inches in width or any combination of measurements that would accommodate the insertion of tie down strapping 15 through each parallel opening.

The upper extremity restraints of the present invention can be sized according to the age of the patient and physical measurements of the patient's upper extremity. Upper extremity restraints may be sized to fit large teenagers and adult patients, toddlers and young children, infants, and newborn patients. Upper extremity restraints in accordance with the present invention, may also be configured for large children, teenagers, elderly, etc.

Embodiments of the present invention may, additionally, be available in assorted colors, including pastels, which may be used to differentiate between the available upper arm restraint sizes, strap lengths, etc. as described above. As appreciated by those skilled in the art, inventive features of the present disclosure are interchangeable on different exemplary embodiments of the present invention, regardless of upper extremity restraint size. The present invention may also be designed for use in a variety of settings. For example, the present invention may be used in veterinary fields for the restraint of animal extremities in animal patients. Additionally, lower extremity restraints are within the scope of the present invention.

Therefore, the following is claimed:

1. A restraining system for restraining a patient upper extremity, having:
    a single substantially rigid oblong board having a length configured to correspond to a length of the upper extremity and a width configured to correspond to a width of the upper extremity, said board defining first and second opposing surfaces and proximal and distal ends;
    wherein the distal end comprises a first bend for accommodating a wrist of said upper extremity, and the proximal end comprises a second backstopping bend for accommodating an elbow of said upper extremity, such that the board can be secured to an upper arm of said upper extremity,
    said first and second opposing surfaces completely comprising hook material, such that the hook material extends across said first bend and said second backstopping bend;
    said system further comprising: a comfort layer dimensioned to correspond to a profile of the patient upper extremity, said comfort layer removably attachable to said hook material of a selected one of said first and second surfaces;
    a distal restraint strap comprising attachment portions at each end, said portions removably attachable to said hook material;
    a proximal restraint strap comprising attachment portions at each end, said portions removably attachable to said hook material;
    wherein the comfort layer may be attached to said selected surface of the board, permitting disposition of the patient's upper extremity upon the comfort layer, and the proximal restraint strap is dimensioned to be slacklessly wrapable over a proximal portion of the patient's upper extremity when attached at each end to arbitrary positions on the first or second board surface opposite the comfort layer, and the distal restraint strap is dimensioned to be slacklessly wrapable over a distal portion of the patient's upper extremity when attached at each end to arbitrary positions on the first or second board surface opposite the comfort layer.

2. The restraining system of claim 1, wherein the first bend effects a bent portion, and the distal restraint strap may be disposed to slacklessly restrain a portion of the upper extremity distal to the wrist to the bent portion.

3. The restraining system of claim 2, wherein the first bend is between 85°-175°.

4. The restraining system of claim 3, wherein the first bend is 135°.

5. The restraining system of claim 1, wherein the second backstopping bend effects a backstop portion disposable behind the elbow of the patient and the proximal restraint strap may be disposed to slacklessly restrain a portion of the upper extremity proximal to the elbow to the backstop portion.

6. The restraining system of claim 5, wherein the second backstopping bend is between 85°-175°.

7. The restraining system of claim 6, wherein the second backstopping bend is 145°.

8. The restraining system of claim 1, wherein the comfort layer comprises resilient padding.

9. The restraining system of claim 8, wherein the comfort layer further comprises a fabric disposed to contact the upper extremity.

10. The restraining system of claim 1, further comprising a tie down strap wherein the tie down strap may be used to secure the board to a patient station.

11. The restraining system of claim 10, wherein the board comprises slots through which the tie down strap may be threaded.

12. The restraining system of claim 1, wherein the first bend effects a hand portion of the board and the second backstopping bend is disposable behind the elbow of the patient, said second backstopping bend effecting a backstop portion of the board, wherein the distal restraint strap may be disposed to slacklessly restrain the hand of the upper extremity to the hand portion and wherein the proximal restraint strap may be disposed to slacklessly restrain the upper arm of the upper extremity to the backstop portion.

13. The restraining system of claim 12, further comprising a middle restraint strap comprising attachment portions at each end, said attachment portions removably attachable to said hook material, wherein the middle restraint strap is dimensioned to be slacklessly disposable around a middle portion of the patient's upper extremity when said middle restraint strap is attached to the first or second board surface opposite the comfort layer.

14. The restraining system of claim 1, wherein the board is perforated.

15. The restraining system of claim 1, wherein the board is formed from moldable thermoplastic.

16. The restraining system of claim 1, wherein the comfort layer is dimensioned to substantially cover one of said first and second surfaces that is anteriorly disposed on the board.

17. The restraining system of claim 1, wherein the comfort layer and board together are of substantially uniform thickness.

18. An upper extremity restraint for maintaining integrity of a patient's intravenous catheter insertion site, having:
    a single substantially rigid oblong backbone with oppositely disposed anterior and posterior surfaces and proximal and distal ends;
    wherein the distal end comprises a first bend for accommodating a wrist of an upper extremity of said patient, and the proximal end comprises a second backstopping bend for accommodating an elbow of said upper extremity, such that the backbone can be secured to an upper arm of said upper extremity;
    the backbone further comprising oppositely disposed longitudinal side edges and exposed hook fastener material covering completely each of said anterior and posterior surfaces thereon, such that the hook fastener material extends across said first bend and said second backstopping bend, said restraint further comprising:

a removably attachable sheet of therapy material comprising loop fastener fabric for fastening to said hook fastener material on said anterior surface, said sheet of therapy material for receiving said patient's forearm thereon, said therapy material defining a contact surface for contacting said patient's forearm, at least two anterior strapping fasteners, comprising:

a first anterior strapping fastener comprising loop fastener fabric removably attachable to said hook fastener material on said posterior surface of said backbone, wherein said first anterior strapping fastener may extend without slack continuously from one of said longitudinal side edges, over said patient's upper extremity and over the other of said longitudinal side edges for securing said backbone to said patient's upper extremity thereon at the proximal end of said backbone, a second anterior strapping fastener comprising loop fastener fabric removably attachable to said hook fastener material on said posterior surface of said backbone, wherein said second anterior strapping fastener may extend without slack continuously from one of said longitudinal side edges, over said patient's upper extremity and over the other of said longitudinal side edges for securing said backbone to said patient's upper extremity thereon at the distal end of said backbone;

whereby the complete coverage of the posterior surface of the backbone with the hook fastener material permits arbitrary attachment points for said first and second anterior strapping fasteners, whereby said upper extremity restraint enables positioning of said patient's upper extremity for secure attachment to a relatively fixed support and thus maintaining integrity of said patient's intravenous catheter insertion.

19. The upper extremity restraint set forth in claim 18, wherein said first bend comprises a 135° bend to accommodate said patient's wrist and said patient's hand of said upper extremity may be secured to said backbone by a third anterior strapping fastener comprised of loop fastener fabric removably attachable to said hook fastener material on said posterior surface of said backbone, wherein said third anterior strapping fastener may extend without slack continuously from one of said longitudinal side edges, over said patient's hand and over the other of said longitudinal side edges for securing said backbone to said patient's hand thereon at the distal end of said backbone.

20. The upper extremity restraint set forth in claim 18, wherein said second backstopping bend comprises a 145° bend disposable at the elbow of said patient and said patient's upper arm may be secured to said backbone by a third anterior strapping fastener comprised of loop fastener fabric removably attachable to said hook fastener material on said posterior surface of said backbone, wherein said third anterior strapping fastener may extend without slack continuously from one of said longitudinal side edges, over said patient's upper arm and over the other of said longitudinal side edges for securing said backbone to said patient's upper arm thereon at the proximal end of said backbone.

21. The upper extremity restraint set forth in claim 18, wherein the backbone comprises pairs of slots through which a tie down strap may be threaded to secure said backbone to a patient station.

22. The reversible upper extremity restraint of claim 18, wherein the sheet of therapy material and backbone together are of substantially uniform thickness.

* * * * *